US012569401B2

(12) United States Patent
Stuart

(10) Patent No.: US 12,569,401 B2
(45) Date of Patent: Mar. 10, 2026

(54) ELONGATE FORM MEDICAMENT CARRIER AND MEDICAMENT DISPENSER

(71) Applicant: Merxin Ltd, King's Lynn (GB)

(72) Inventor: Adam Stuart, King's Lynn (GB)

(73) Assignee: Merxin Ltd, King's Lynn (GB)

( * ) Notice: Subject to any disclaimer, the term of this patent is extended or adjusted under 35 U.S.C. 154(b) by 918 days.

(21) Appl. No.: 17/782,303

(22) PCT Filed: Dec. 2, 2020

(86) PCT No.: PCT/IB2020/061363
§ 371 (c)(1),
(2) Date: Jun. 3, 2022

(87) PCT Pub. No.: WO2021/111318
PCT Pub. Date: Jun. 10, 2021

(65) Prior Publication Data
US 2023/0023547 A1 Jan. 26, 2023

(30) Foreign Application Priority Data
Dec. 6, 2019 (GB) ...................................... 1917890

(51) Int. Cl.
*A61J 1/03* (2023.01)
*A61M 15/00* (2006.01)
(52) U.S. Cl.
CPC .......... *A61J 1/035* (2013.01); *A61M 15/0003* (2014.02); *A61M 15/0043* (2014.02); *A61M 15/0051* (2014.02); *A61M 15/0055* (2014.02)
(58) Field of Classification Search
CPC .... B65D 75/32; B65D 75/325; B65D 75/327; B65D 75/36; B65D 75/367;
(Continued)

(56) References Cited

U.S. PATENT DOCUMENTS 6,375,956 B1 * 4/2002 Hermelin ............ B65D 75/327
424/464
7,151,456 B2 12/2006 Godfrey
(Continued)

FOREIGN PATENT DOCUMENTS

CA 2767306 A1 * 1/2011 ........ A61M 15/0031
EP 2082760 A1 * 7/2009 ........ A61M 15/0036
(Continued)

OTHER PUBLICATIONS

Combined Search and Examination Report under Section 17 and 18(3) issued in GB Patent Application GB1917890.4, on Feb. 26, 2020, 6 pages.
(Continued)

*Primary Examiner* — Kathryn E Ditmer
(74) *Attorney, Agent, or Firm* — Ziegler IP Law Group, LLC.

(57) ABSTRACT

Disclosed is an elongate form medicament carrier and a medicament dispenser. The medicament carrier has a first end, a second end, and a central portion, and carrying multiple distinct medicament dose portions, the medicament dose portions consisting of a first set and a second set of medicament dose portions, the first set of medicament dose portions distributed in a first portion of the elongate form medicament carrier between the first end and the central portion of the elongate form medicament carrier and containing a medicament active, or a mixture of medicament actives, and the second set of medicament dose portions distributed in a second portion of the elongate form medicament carrier between the second end and the central portion of the elongate form medicament carrier and containing a medicament active, or a mixture of medicament actives, wherein the dose portions in the second set of
(Continued)

medicament dose portions are different from the dose portions in the first set of medicament dose portions.

20 Claims, 5 Drawing Sheets

(58) Field of Classification Search
CPC ........ B65D 2075/362; A61M 15/0003; A61M
15/0043; A61M 15/0051; A61M 15/0055;
A61J 1/035; B65B 11/52; B65B 9/04–045
See application file for complete search history.

(56) References Cited

U.S. PATENT DOCUMENTS

| | | | |
|---|---|---|---|
| 8,161,958 B2 | 4/2012 | Johnson et al. | |
| 8,201,556 B2 | 6/2012 | Jones et al. | |
| 8,511,304 B2 * | 8/2013 | Anderson ......... | A61M 15/0068 |
| | | | 128/200.14 |
| 8,534,281 B2 | 9/2013 | Davies et al. | |
| 9,333,310 B2 | 5/2016 | Jones et al. | |
| 2003/0102247 A1 * | 6/2003 | Inoue ...................... | A61J 1/035 |
| | | | 206/532 |
| 2006/0196504 A1 * | 9/2006 | Augustyn ......... | A61M 15/0045 |
| | | | 128/203.15 |
| 2007/0295332 A1 * | 12/2007 | Ziegler ............. | A61M 15/0028 |
| | | | 128/203.15 |
| 2009/0230013 A1 | 9/2009 | Born et al. | |
| 2012/0145739 A1 * | 6/2012 | Doyle ................. | B65D 75/327 |
| | | | 225/56 |
| 2015/0174004 A1 * | 6/2015 | Miyamoto ........... | B65D 75/367 |
| | | | 206/532 |
| 2021/0316091 A1 * | 10/2021 | Cottenden ........ | A61M 15/0055 |
| 2021/0322686 A1 * | 10/2021 | Cottenden ........ | A61M 15/0003 |

FOREIGN PATENT DOCUMENTS

| | | | | |
|---|---|---|---|---|
| GB | 2380728 A | * | 4/2003 | ................ A61J 1/03 |
| WO | 2000064778 A1 | | 11/2000 | |
| WO | 2001060695 A1 | | 8/2001 | |
| WO | 03061743 A1 | | 7/2003 | |
| WO | 2004026378 A2 | | 4/2004 | |
| WO | 2006019760 A1 | | 2/2006 | |
| WO | 2006093784 A2 | | 9/2006 | |
| WO | 2008060964 A2 | | 5/2008 | |
| WO | 2008077068 A1 | | 6/2008 | |
| WO | 2020053878 A1 | | 3/2020 | |

OTHER PUBLICATIONS

International Search Report and Written Opinion of the International Searching Authority mailed in PCT Patent Application PCT/IB2020/061363 on Mar. 15, 2021, 14 pages.

Written Opinion of the International Preliminary Examining Authority mailed in PCT Patent Application PCT/IB2020/061363 on Jun. 11, 2021, 10 pages.

Notification of Transmittal of the International Preliminary Report on Patentability mailed in PCT Patent Application PCT/IB2020/061363 on Feb. 14, 2022, 22 pages.

* cited by examiner

ELONGATE FORM MEDICAMENT CARRIER AND MEDICAMENT DISPENSER

TECHNICAL FIELD

The present disclosure relates generally to a medicament carrier for administering medicament doses to patients; and more specifically, to elongate form medicament carriers for medicament dose portions and medicament dispensers.

BACKGROUND

In recent past, developments in medical industry have led to formulation of new medicines and devices tailored for diseases and abnormalities such as asthma and other pulmonary illnesses. Exponentially increasing pollution levels reverberates the already ravaging pulmonary disease toll to a huge extent. Currently, there exists a plurality of therapeutic options for asthma and chronic obstructive pulmonary disease (COPD). In case of asthma, inhaled corticosteroids (ICS) are the cornerstone of maintenance therapy, and for symptomatic asthma patients, ICS along with a long-acting beta2-adrenergic agonist (LABA) is generally prescribed. In COPD, an inhaled long-acting bronchodilator (a LABA or a long-acting muscarinic receptor antagonist [LAMA]) is used as maintenance therapy for patients who are symptomatic and are using rescue medication alone.

In certain circumstances, it is desirable to have a medicament dispenser that contains each active component or mixture thereof of a combination product in an isolated state and at the same time enables the delivery of combined dosage against a minimum number of patient actions. Particularly, it is desirable for all active components of the combined dosage to be delivered to the patient in a single, combined dosage as a response to a single patient dosing action.

Typically, to perform such a function, COPD patients are administered combination treatment either as a distinct combination (i.e. multi-active) medicament product, which comprise a defined mixture of each component medicament, or as groups of single active medicament products, which are designed to be taken in combination or sequentially. Whilst combination products offer added convenience to the patient, certain medicament actives are difficult to formulate as distinct combination products. Such medicament actives may undergo undesired chemical interaction upon formulation.

Conventionally, medicament dispensers used to administer combination treatment comprises plurality of elongated form carriers. The plurality of carriers along with sections for separate storage of the blister strip results in added mechanical complexity and additional componentry to the medicament dispenser. These factors also contribute to an increase in tendency of mechanical failure for such medicament dispensers. Furthermore, multiple carriers contribute to additional space occupation, reduce device compactness and negatively impacts ease of device assembly. Notably, added componentry to the medicament device increases the overall device cost and feasibility of production.

Therefore, in light of the foregoing discussion, there exists a need to overcome the aforementioned drawbacks of the current medicament dispensers and provide an efficient, reliable, cost-effective and easy-to-use medicament dispenser.

SUMMARY

The present disclosure seeks to provide an elongate form medicament carrier. The present disclosure also seeks to provide a medicament dispenser comprising the elongate form medicament carrier. The present disclosure seeks to provide a solution to the existing problem of high-cost, complexity, and high rate of failure of conventional medicament carriers and dispensers. An aim of the present disclosure is to provide a solution that overcomes at least partially the problems encountered in prior art, and provides a simple, reliable, robust medicament carrier and dispenser for the delivery of multiple distinct medicament doses in a single combined dosage employing a single command action.

In one aspect, an embodiment of the present disclosure provides an elongate form medicament carrier having a first end, a second end, and a central portion extending across the width of the elongate form medicament carrier, and carrying multiple distinct medicament dose portions, the medicament dose portions consisting of a first set and a second set of medicament dose portions, the first set of medicament dose portions distributed in a first portion of the elongate form medicament carrier between the first end and the central portion of the elongate form medicament carrier and containing a medicament active, or a mixture of medicament actives, and the second set of medicament dose portions distributed in a second portion of the elongate form medicament carrier between the second end and the central portion of the elongate form medicament carrier and containing a medicament active, or a mixture of medicament actives wherein the dose portions in the second set of medicament dose portions are different from the dose portions in the first set of medicament dose portions.

Optionally, the dose portions in the second set of medicament dose portions differ from the dose portions in the first set of medicament dose portions in that the dose portions in the second set of medicament dose portions contain a medicament active, or a mixture of medicament actives that is different from that in the first set of medicament dose portions.

In another aspect, an embodiment of the present disclosure provides a medicament dispenser comprising a supply of drug, the supply of drug consisting of one elongate form medicament carrier, said dispenser having a dispensing mechanism which is adapted to operate, upon each actuation of the dispenser, to dispense a single distinct medicament dose portion from each of said first and second sets of medicament dose portions, said mechanism comprising, a. at least one receiving station receiving portions of the elongate form medicament carrier respectively carrying each of the first and second sets of medicament dose portions;

b. a release for releasing a distinct medicament dose portion from each of the portions of the elongate form medicament carrier respectively carrying each of the first and second sets of medicament dose portions;

c. an outlet, positioned to be in communication with the distinct medicament dose portions releasable by said release to enable their dispensing to the patient; and d. at least one indexer for individually indexing the distinct medicament dose portions of each of the portions of the elongate form medicament carrier respectively carrying each of the first and second sets of medicament dose portions.

Embodiments of the present disclosure substantially eliminate or at least partially address the aforementioned problems in the prior art, and enable delivery of multiple distinct medicament doses in a single combined dosage whilst reducing complexity and componentry of the medicament dispenser Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
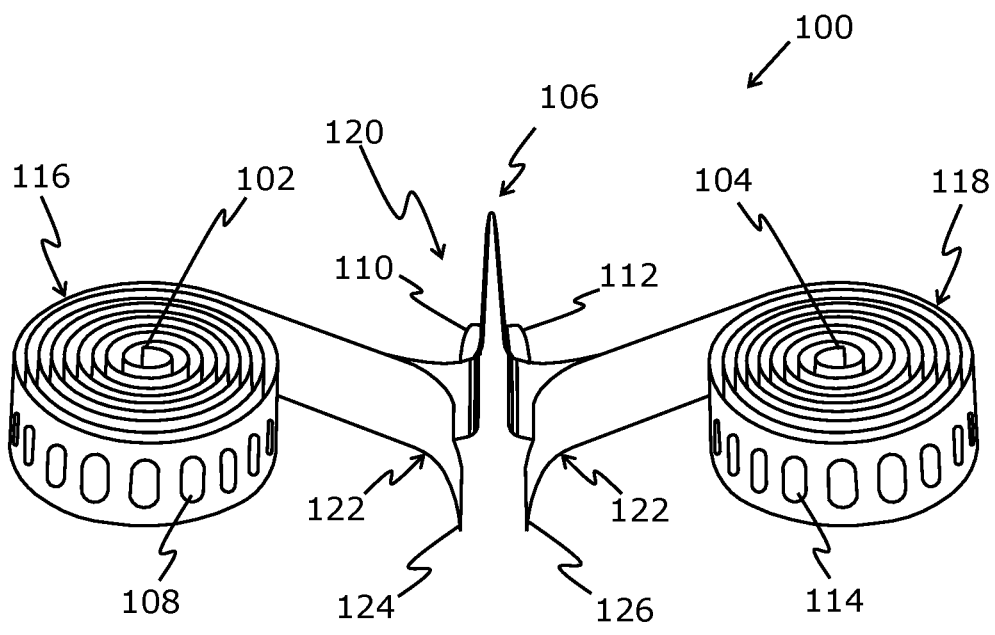
FIGS. 1A and 1B are perspective views of an elongate form medicament carrier, in accordance with different embodiments of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

The present disclosure provides an elongate form medicament carrier and a medicament dispenser comprising the elongate form medicament carrier as a supply of the drug. The elongate form medicament carrier stores the medicament actives of the combination product to be administered to the patient separately and enables delivery of a combined medicament dose in response to a minimum number of patient actions. The elongate form medicament carrier and the medicament dispenser provide an innovative and cost-effective alternative to the conventional multiple elongate form carriers. Notably, employing a single medicament carrier carrying different medicament dose portions on different ends imparts feasibility in manufacturing, filling and storage processes. Furthermore, the single elongate form medicament carrier reduces device componentry of the medicament dispenser dispensing the medicament dose portions, thereby reducing complexity and overall cost of the medicament dispenser. Moreover, the single elongate form medicament carrier is assembled into the medicament dispenser with relatively greater ease, thereby simplifying the assembly of the medicament dispenser and reducing the mechanisms required to drive the dispensing mechanism during use. Specifically, the single elongate form medicament carrier only requires a single take-up spool for winding of the used portions of the medicament carrier. Such reduced componentry reduces the risk of mechanical failure or jamming. Additionally, employing the single elongate form medicament carrier enables filling of both the medicament dose portions simultaneously, reducing the amount of labelling, tracking and pairing of the medicament dose portions whilst manufacturing and assembling.

Pursuant to embodiments of the present disclosure, there is provided a medicament carrier operable to administer a medicament formulation or a medicament product to an intended user for example, a patient suffering from respiratory illnesses. Such medicament carriers can be employed to administer a plurality of medicaments useful for a variety of conditions such as asthma, pulmonary diseases such as COPD (chronic obstructive pulmonary disease). The medicament carrier is further operable to carry a plurality of distinct medicament dose portions and shaped in an elongated form so as to accommodate the distinct elements of the medicament carrier.

It will be appreciated that the first portion and the second portion of the elongate form medicament carrier define two separate areas, wherein the central portion is provided between the first portion and the second portion.

Optionally, to store the medicament dose portions, multiple distinct regions may be defined on the elongate form medicament carrier. The elongate form medicament carrier may comprise of a pair of elongate sheets that have been attached together, wherein one of the pair of elongate sheets provides regions in which the medicament dose portions can be stored.

It will be appreciated that the dose portions in the second set of medicament dose portions are different from the dose portions in the first set of medicament dose portions. In an embodiment, the dose portions in the second set of medicament dose portions differ from dose portions in the first set of medicament dose portions in that the dose portions in the second set of medicament dose portions comprise a different amount (namely, a higher amount or a lower amount) of the medicament active (or a mixture of medicament actives) than in the dose portions of the first set of medicament dose portions. Additionally or alternatively, optionally, the dose portions in the second set of medicament dose portions differ from the dose portions in the first set of medicament dose portions in that the dose portions in the second set of medicament dose portions contain a medicament active, or a mixture of medicament actives that is different from that in the first set of medicament dose portions.

In an embodiment, the elongate form medicament carrier comprises an unsplit elongate sheet as one of the pair of elongate sheets employed to form the elongate form medicament carrier. Herein, the unsplit elongate sheet is implemented as either of the base elongate sheet or the lid elongate sheet. In an instance, the unsplit elongate sheet is implemented as the base elongate sheet. In such instance, the lid elongate sheet may be peeled, punctured, ruptured or torn to expose the medicament dose portion in the base elongate sheet to be administered to the patient.

Optionally, the elongate form medicament carrier further comprises a split elongate sheet substantially secured to the unsplit elongate sheet. Herein, the split elongate sheet when substantially secured to the unsplit elongate sheet enables storing of the medicament dose portions therebetween, wherein the split elongate sheet is peeled apart from the unsplit elongate sheet to expose the medicament dose portion stored therein. Notably, the combination of the split elongate sheet and the unsplit elongate sheet may be implemented in a manner similar to a conventional blister strip, wherein the medicament dose portions are stored in the blisters (or pockets) on the blister strip. The unsplit elongate sheet and the split elongate sheet have respective central portions, wherein the central portions do not comprise any regions (e.g. blisters) to store the medicament dose portions. The unsplit elongate sheet and the split elongate sheet have first portions corresponding to the first set of medicament dose portions, and second portions corresponding to the second set of medicament dose portions. It will be appreciated that the first portions and second portions of the unsplit and split elongate sheet lie on either side of the central portions thereof. Therefore, the first portions of the split elongate sheet and unsplit elongate sheet correspond to the first end of the elongate form medicament carrier. Similarly, the second portions of the split elongate sheet and unsplit elongate sheet correspond to the second end of the elongate form medicament carrier. The central portion of the split elongate sheet and unsplit elongate sheet correspond to the central portion of the elongate form medicament carrier. The central portion of the split elongate sheet may be divided, wherein the first inner end is proximate to the first portion of the split elongate sheet and the second inner end is proximate to the second portion of the split elongate sheet. As mentioned, the first inner end and the second inner end are not secured to the unsplit elongate sheet and therefore, the first inner end and the second inner end provide a structure similar to a lift-tab for peeling the split elongate sheet from the unsplit elongate sheet to expose the medicament dose portions. It will be appreciated that the first inner end of the split elongate sheet is used to peel and expose the first set of medicament dose portions and similarly, the second inner end of the split elongate sheet is used to peel and expose the second set of medicament dose portions. The lift-tabs provided may be harnessed to a dispensing mechanism, such as bobbins, to wind on the elongate medicament carrier, specifically the split elongate sheet. Notably, either the split elongate sheet is the lid elongate sheet and the unsplit elongate sheet is the base elongate sheet; or the split elongate sheet is the base elongate sheet and the unsplit elongate sheet is the lid elongate sheet.

Optionally, a first set and a second set of multiple distinct pockets (or recesses) are defined between the base elongate sheet and the lid elongate sheet and containing medicament respectively consisting of the first set of medicament dose portions and the second set of medicament dose portions. Furthermore, the elongate sheet that comprises pockets formed therein is referred to as a "base elongate sheet" and the elongate sheet covering the pockets defined in the base elongate sheet is referred to as a "lid elongate sheet". Notably, the first set of multiple distinct pockets corresponding to the first set of medicament dose portions are defined on the first portion of base elongate sheet (namely, one of the split elongate sheet or unsplit elongate sheet). Similarly, the second set of multiple distinct pockets corresponding to the second set of medicament dose portions are defined on the second portion of base elongate sheet (namely, one of the split elongate sheet or unsplit elongate sheet). Furthermore, said first set of pockets is spaced along the length of the first portion of the elongate form medicament carrier and said second set of pockets is spaced along the length of the second portion of the elongate form medicament carrier. The first set of pockets may be distributed in the first portion of the elongate form medicament carrier. Similarly, the second set of pockets may be distributed in the second portion of the elongate form medicament carrier.

Optionally, the multiple distinct pockets are formed in the base elongate sheet, and the lid elongate sheet is hermetically sealed to the base elongate sheet except in the region of the pockets and the inner ends of the lid elongate sheet or the base elongate sheet, as applicable, in such a manner that the lid elongate sheet and the base elongate sheet can be peeled apart. As mentioned previously, the split elongate sheet is substantially secured to the unsplit elongate sheet. Notably, the split elongate sheet is not secured to unsplit elongate sheet in the regions of the first and second set of pockets and at the first inner end and second inner end of the split elongate sheet. The sealing of the medicament dose portions implemented between the lid elongate sheet and the base elongate sheet ensures isolation of medicament dose portions from external factors such as humidity, dust particles, pathogens and so forth, and, if necessary, sterility of the medicament dose portions.

Optionally, said lid elongate sheet comprises at least the following successive layers: (a) paper; adhesively bonded to (b) polyester; adhesively bonded to (c) aluminium foil; that is coated with a heat seal lacquer for bonding to the base elongate sheet. Optionally, the base elongate sheet comprises at least the following successive layers: (a) oriented polyamide (OPA); adhesively bonded to (b) aluminium foil; adhesively bonded to (c) a third layer comprising a polymeric material. Notably, a multi-layered construction of the lid and base elongate sheets implemented using a combination of metal, paper and polymeric materials ensures a strong and reliable implementation of the lid and base elongate sheet and provides a superior barrier layer between the external contaminants and the medicament dose portions. Furthermore, the heat seal lacquer used to seal the lid elongate sheet to the base elongate sheet provides a sturdy hermetic sealing between the lid elongate sheet and the base elongate sheet.

Optionally, the first portion of the elongate form medicament carrier is substantially the same size and shape as the second portion of the elongate form medicament carrier. Specifically, the elongate form medicament carrier is substantially symmetric across the central portion of the elongate form medicament carrier. It will be appreciated that the first portion of the split and unsplit elongate sheet (corresponding to first set of medicament dose portions) has a substantially same length as the second portion of the split and unsplit elongate sheet (corresponding to the second set of medicament dose portions).

Optionally, the multiple distinct medicament dose portions of each of the first portion and the second portion of the elongate form medicament carrier are uniformly spaced. Notably, the distance between dose portions of the first set of multiple distinct pockets defined between the base elongate sheet and the lid elongate sheet is uniform. Similarly, the distance between dose portions of the second set of multiple distinct pockets defined between the base elongate sheet and the lid elongate sheet is uniform.

In an embodiment, the spacing of the multiple distinct medicament dose portions of the first portion of the elongate form medicament carrier is equivalent to the spacing of the multiple distinct medicament dose portions of the second portion of the elongate form medicament carrier. Specifically, the spacing between the first set of multiple distinct pockets defined between the base elongate sheet and lid elongate sheet is equivalent to the spacing between the second set of multiple distinct pockets. As mentioned previously, the first portion of the split and unsplit elongate sheet (corresponding to first set of medicament dose portions) has a substantially same length as the second portion of the split and unsplit elongate sheet (corresponding to the second set of medicament dose portions). Since the spacing between the first set of multiple distinct pockets and second set of multiple distinct pockets is equivalent; and the length of the first portion of the split and unsplit elongate sheet is equivalent to the length of the second portion of the split and unsplit elongate sheet, it will be understood that the number (namely, count) of first set of multiple distinct pockets is equal to number of second set of multiple distinct pockets.

In another embodiment, the spacing of the multiple distinct medicament dose portions of the first portion of the elongate form medicament carrier is different to the spacing of the multiple distinct medicament dose portions of the second portion of the elongate form medicament carrier. Therefore, as explained previously, in such embodiment, the number (namely, count) of first set of multiple distinct pockets is different in comparison with number of second set of multiple distinct pockets.

Optionally, the length of the central portion is greater than the spacing of the multiple distinct medicament dose portions of both the first and the second portions of the elongate form medicament carrier. More optionally, the length of the central portion of the elongate form medicament carrier is significantly greater than the spacing between adjacent pockets in the first set of multiple distinct pockets and in the second set of multiple distinct pockets. Thus, the length of the central portions of the split and unsplit elongate sheet is significantly greater than the spacing between adjacent pockets in either set of the multiple distinct pockets defined between the base elongate sheet and the lid elongate sheet.

Throughout the present disclosure, the term "medicament active" refers to a pharmaceutical compound or a drug administered to a patient for healing, treating, altering, improving, restoring, relieving, and/or curing a particular condition, disease, or mental or physical state. Notably, a medicament active includes an active ingredient or a combination of active ingredients and inactive ingredients, optionally mixed with an excipient or dissolved in some other carrier for delivery to the patient. Furthermore, the mixture of medicament active comprises a plurality of pharmaceutical compounds, wherein the plurality of pharmaceutical compounds do not react with each other. Furthermore, the medicament active is administered to the patient in a measured quantity that is a whole number multiple of the quantity referred to herein as the "medicament dose portion". Usually, the administered dose can be provided in one medicament dose portion.

Optionally, the medicament dose portions are in powdered or solid form.

More optionally, the medicament active in the medicament dose portions may consist essentially of particles less than 10 microns in diameter, such that the non-agglomerated medicament active particles have a mass median diameter less than 10 microns, preferably less than 5 microns. According to an embodiment, each medicament dose portion of each portion of the elongate form medicament carrier comprises a single active medicament component.

Optionally, said single active medicament components are selected from the group consisting of vilanterol, salmeterol, fluticasone propionate, formoterol, budesonide, tiotropium, aclidinium, umeclidinium, glycopyrronium, indacaterol and olodaterol and salts or solvates thereof.

Optionally, each of the first set of medicament dose portions comprises a bronchodilator as the active medicament component and each of the second set of medicament dose portions comprises an anti-inflammatory as the active medicament component. Notably, the bronchodilator as the active medicament component is employed for dilating bronchi and bronchioles of the patient it is administered to and for increasing airflow to the lungs. Furthermore, the anti-inflammatory as the active medicament component in the second set of medicament dose portions is employed for reducing swelling in the patient, decrease airway sensitivity caused by inflammation and reduce mucus production. A combination of medicament dose portion comprising bronchodilator and anti-inflammatory is generally administered to patient suffering from asthma.

Optionally, said bronchodilator is a long-acting beta-agonist and/or a long-acting muscarinic receptor agonist and said anti-inflammatory is a steroid.

According to another embodiment, each medicament dose portion of at least one set of medicament dose portions comprises plural active medicament components. Notably, the first set of medicament dose portions may comprise a mixture of medicament actives comprising plural active medicament components. Also, the second set of medicament dose portions may comprise a mixture of medicament actives comprising plural active medicament components, wherein at least one active medicament component in the second set of medicament dose portions is different from the plural active medicament components in the first set of medicament dose portions.

Pursuant to embodiments of the present disclosure, there is provided a medicament dispenser comprising a supply of drug, the supply of drug consisting of one elongate form medicament carrier as described herein above. The medicament dispenser has a dispensing mechanism which is adapted to operate, upon each actuation of the dispenser, to dispense a single distinct medicament dose portion from each of said first and second sets of medicament dose portions. Specifically, the medicament dispenser is employed by a patient to administer a single distinct medicament dose portion from each of said first and second sets of medicament dose portions stored in the elongate form medicament carrier, wherein the patient employs the dispensing mechanism to cause the actuation of the dispenser. It will be appreciated that a single distinct medicament dose portion from each of the first and second sets of medicament dose portions is administered as a mixture of the medicament active (or a mixture of medicament actives) in the first medicament dose portion and the medicament active (or a mixture of medicament actives) in the second medicament dose portion.

In regards to the medicament dispenser described above comprising the dispensing mechanism, the dispensing mechanism comprises, a. at least one receiving station receiving portions of the elongate form medicament carrier respectively carrying each of the first and second sets of medicament dose portions;

b. a release for releasing a distinct medicament dose portion from each of the portions of the elongate form medicament carrier respectively carrying each of the first and second sets of medicament dose portions;

c. an outlet, positioned to be in communication with the distinct medicament dose portions releasable by said release to enable their dispensing to the patient; and d. at least one indexer for individually indexing the distinct medicament dose portions of each of the portions of the elongate form medicament carrier respectively carrying each of the first and second sets of medicament dose portions.

The medicament dispenser comprises at least one receiving station for receiving portions of the elongate form medicament carrier. Specifically, the at least one receiving station may be implemented as at least one capstan. The dose portions may be stored in pockets formed in a base elongate sheet and protected (namely, covered) by a lid elongate sheet. The at least one receiving station may comprise a recess in the at least one capstan that registers (or positions) the pocket adjacent to the outlet. Specifically, the at least capstans comprises recesses for accommodating pockets of the elongate form medicament carrier and the capstan positions a given pocket adjacent to the outlet for delivery thereof. Alternatively, the dose portion may be adhered to a surface of the elongate form medicament carrier in a region that can be encompassed by the outlet, and the at least one receiving station comprises at least one capstan configured to bring the dose portion into registration with the outlet, ideally directly adjacent the outlet. Optionally then, the dose portion may be protected by a lid elongate sheet in the form of a liner, i.e. not strongly adhered to the base elongate sheet, but readily peeled therefrom.

Optionally, a common receiving station receives each of the first and second portions to the elongate form medicament carrier. Specifically, the at least one receiving station is implemented as a common receiving station, wherein each of the first and second portions of the elongate form medicament carrier are received thereby.

Alternatively, optionally, plural distinct receiving stations receive respective portions of first and second portions to the elongate form medicament carrier. Specifically, the at least one receiving station is implemented as plural distinct receiving stations. In an example, the at least one receiving station is implemented as a pair of capstans, wherein a first capstan of the pair receives the first portion of the elongate form medicament carrier and a second capstan of the pair receives the second portion of the elongate form medicament carrier. The capstans are in the form of dimpled cylinders, and pockets of the elongate medicament carrier may be carried in the dimples upon rotation of the capstan in order to advance a dose.

As mentioned previously with respect to the medicament dispenser, the dispensing mechanism comprises the release for releasing a distinct medicament dose portion from each of the portions of the elongate form medicament carrier respectively carrying each of the first and second sets of medicament dose portions. Notably, the release enables release of each of the first and second sets of medicament dose portions into the outlet, so that the it can be administered to the patient. It will be appreciated that the release is triggered by an actuation means on the medicament dispenser, wherein the patient uses the actuation means to cause actuation of the medicament dispenser and release each of the first and second sets of medicament portions. In an embodiment, the actuation means is implemented as a button, wherein the patient presses the button to trigger the release. In another embodiment, the actuation means is implemented as a slider, wherein the patient slides the slider to trigger the release.

Optionally, said release comprises means to access medicament carried by said medicament carrier by a rupturing, puncturing, tearing or peeling action. Specifically, as aforementioned the elongate form medicament carrier comprises first and second sets of medicament dose portions, wherein each single distinct medicament dose portion is sealed thereon. Therefore, to release the medicament portion from the elongate form medicament carrier, an action such as rupturing, puncturing, tearing or peeling needs to be performed depending upon the type of the elongate form medicament carrier and the type of medicament dispenser. Such action by the release discharges the medicament doses carried by the elongate form medicament carrier enabling the administration of the medicament to the patient. The released dose may temporarily be retained on the elongate form medicament carrier until dispensed therefrom. Thus, the release may occur before the dose is fully registered by the at least one receiving station.

Optionally, in an instance when the elongate form medicament carrier is implemented as a peelable blister strip form medicament carrier, said release comprises a peeler for peeling apart the peelable blister strip form medicament carrier. Specifically, the peeler separates the split elongate sheet from the unsplit elongate sheet to release the medicament dose portions contained in the first and second set of multiple distinct pockets defined between the split elongate sheet and the unsplit elongate sheet. It will be appreciated that the release is configured to release the first set of the medicament dose portions from the first portion of the elongate form medicament carrier and the second set of medicament dose portions from the second portion of the elongate form medicament carrier. In an instance when the release provides the peeling action, the at least one receiving station may comprise a stationary blade that is positioned between already separated portions of the base elongate sheet and the lid elongate sheet. As the elongate form medicament carrier is wound on, the blade progressively separates further portions of the lid elongate sheet from the base elongate sheet by providing diverging paths either side of the blade.

Optionally, in an instance, when the release provides a puncturing action, the receiving station may comprise a revolving punch. Such a punch may puncture a hole in the lid elongate sheet in line with a dose portion before that dose portion is registered with the outlet. Alternatively, the dose portion may be registered with the outlet, and subsequently the punch may provide a through hole piercing the base elongate and lid elongate sheet to provide a through passage. The dose may then be delivered in an airstream, which is typically provided when the patient inhales through the medicament dispenser, through the through passage.

The dispensing mechanism of the medicament dispenser further comprises an outlet, positioned to be in communication with the distinct medicament dose portions releasable by said release to enable their dispensing to the patient. Specifically, upon release, the distinct medicament dose portion from each of the first and second portion of the elongate form medicament carrier is received by the outlet, wherein the patient uses the outlet of the medicament dispenser to receive the medicament dose portions. In an example, the patient may apply suction to the medicament dose portions through the outlet.

Optionally, the outlet provides access between a compartment of the medicament dispenser housing the elongate form medicament carrier and a chamber for mixing a dispensed dose with an airstream for delivery to a patient. Specifically, when the patient applies a suction to a mouthpiece or a nose piece of the medicament dispenser, due to the change in pressure, an airstream (namely, an airflow) is introduced into the medicament dispenser. Such airstream may carry the medicament dose portions from the outlet (or from the elongate form medicament carrier) to the patient. Optionally, there are two outlets, one for each of the first and second sets of medicament dose portions. Advantageously, the elongate form medicament carrier is practically airtight around the opening, in order to control airflow to the medicament dose portion to dispense it.

Optionally, a single common outlet passage is provided, which communicates with the distinct medicament dose portions via respective outlets. Notably, a single distinct medicament portion from each of the first and second set of medicament dose portions is received into the single common outlet passage, whereby the patient receives a mixture of each one of the first set and second set of medicament dose portions is received via a mouthpiece or nosepiece (not shown).

Optionally, said common outlet passage is shaped to encourage mixing of said released medicament dose portions. Specifically, the bottom of the said single common outlet passage is configured as a pair of converging inclined surfaces, each containing an outlet, wherein such relative orientation of the outlets encourages the single distinct medicament dose portions from each of the first and second set of medicament dose portions to mix with each other.

In an exemplary embodiment, in which the dose portions are in pockets, a pocket of the base elongate sheet is registered sealingly adjacent an outlet. Herein, the outlet is divided into an inlet portion and an outlet portion. The outlet portion is configured in communication with a mouthpiece or nosepiece of the medicament dispenser via an outlet passage, and the inlet portion is configured in communication with an external inlet via an inlet passage that allows air to be drawn into the device due to suction applied by the patient on the mouthpiece or nosepiece. Optionally, a by-pass airflow may be provided linking the inlet passage with the outlet passage, so that some of the airstream by-passes the pocket. In use, the airstream from the inlet passage enters the pocket through the inlet portion of the outlet. Consequently, the airstream scours the contents (the dose) of the pocket, hence dispensing the dose, and carries it via the outlet portion of the outlet, along the outlet passage to the patient.

The dispensing mechanism of the medicament dispenser further comprises at least one indexer for individually indexing the distinct medicament dose portions of each of the portions of the elongate form medicament carrier respectively carrying each of the first and second sets of medicament dose portions. Notably, the at least one indexer is configured on the medicament dispenser to provide a count of the number of medicament dose portions from the first and second set of medicament dose portions that have been administered to the patient (or, have been released from the medicament dispenser). Herein, the at least one indexer is coupled to the aforementioned release, wherein the at least one indexer indexes a change in count of administered medicament dose portions as the medicament dose portions are released by the release. The at least one indexer enables a patient to (a) keep a count of the number of medicament dose portions that have been administered to them, and (b) determine whether the medicament dose portions have been released from the elongate form medicament carrier and are ready to be taken up, as the number on the at least one indexer changes as soon as the medicament dose portions have been released by the release. The indexer may comprise an arrangement of gears driven by a predefined extent of travel per dose. Notably, the arrangement of gears is configured to register that the dose(s) have been dispensed upon exit of a specific length of the elongate sheets from the at least one receiving station. In a simplified implementation of the medicament dispenser, the at least one indexer employs a mechanical counter, typically comprising a series of disks mounted on an axle, with the digits zero through nine marked on edges of the disks, to keep count of the medicament dose portions released from the elongate form medicament carrier. Alternatively, optionally, the at least one indexer is implemented as a digital counter.

Optionally, a single indexer indexes the first and second sets of medicament dose portions. Specifically, a single indexer is employed in the medicament dispenser in an instance the first and second sets of medicament dose portions are always released and administered to the patient simultaneously. It will be appreciated that since the first and second sets of medicament portions are released from the elongate form medicament carrier simultaneously every time, the number of administered medicament dose portions for the first set and second set will always be the same. Therefore, a single indexer is employed to index release of the first and second sets of the medicament dose portions.

Optionally, plural distinct indexers index the first and second sets of medicament dose portions. Specifically, plural (namely, a pair of) distinct indexers are employed in an instance when the first and second sets of medicament dose portions are not always released simultaneously. In an instance, one medicament dose portion from the second set of the medicament dose portions is administered for every two medicament dose portions administered from the first set of medicament dose portions. In other words, a medicament dose portion from the second set of medicament dose portions is released for every alternate medicament dose portion released from the first set of medicament dose portions. Therefore, since the count of medicament dose portions released from the first and second set of medicament dose portions is different, distinct indexers are employed to index the first and second sets of medicament dose portions. Optionally, said plural distinct indexers are mutually coupled. Notably, the plural distinct indexers are coupled such that the count shown by the indexers is in tandem with the medicament dose portions released from the first set and second set of medicament dose portions.

In an embodiment, the medicament dispenser further comprises a take-up spool configured to wind the unsplit elongate sheet onto the take-up spool as the take-up spool is rotated, starting with the central portion and continuing to wind the first and second portions of the unsplit elongate sheet onto the take-up spool after dispensing doses from the first and second sets of medicament portions respectively. In an instance, the unsplit elongate sheet is implemented as the base elongate sheet, wherein the lid elongate sheet is punctured to expose the medicament dose portions for administration. Herein, after the medicament dose portions have been delivered from the elongate form medicament carrier, the unsplit elongate sheet along with the punctured lid elongate sheet is wound onto the take-up spool. In another instance, the unsplit elongate sheet and the split elongate sheet are peeled apart by the release (as described herein above) to dispense the medicament portions carried by the elongate form medicament carrier in the first and second portion thereof. Therefore, the take-up spool rotates and winds the unsplit elongate sheet as the split elongate sheet is peeled off therefrom. The mechanism of the take-up spool is triggered by the actuation means triggering the release. Specifically, the actuating means (such as a button or slider) may trigger the rotation of the take-up spool such that the unsplit elongate sheet is wound up around the take-up spool. Optionally, the rotation motion of the take-up spool enables the peeling apart of the split elongate sheet from the unsplit elongate sheet.

Optionally, the central portion of the elongate form medicament carrier is secured to the take-up spool. Notably, the central portion of the elongate form medicament carrier is secured to the take-up spool, wherein the unsplit elongate sheet continues to wind around the take-up spool starting with the central portion of the elongate form medicament carrier.

Optionally, the central portion of the elongate form medicament carrier is secured to the take-up spool by a peg. Specifically, the peg is implemented as a short pin or bolt, around which the central portion of the elongate form medicament carrier is secured.

In another embodiment, the medicament dispenser comprises a roller with roller grips configured to wind the unsplit elongate sheet into a waste space of the medicament dispenser, starting with the central portion of the elongate form medicament carrier and continuing to wind the first and second portions of the unsplit elongate sheet into the waste space after dispensing doses from the first and second sets of medicament portions respectively. Specifically, the roller comprises a pair of roller grips that direct the central portion and the first and second portions of the elongate form medicament carrier into the waste space configured in the medicament dispenser below the at least one receiving station. The waste space is configured in a manner that it can accommodate a substantial portion of unsplit elongate sheet of the elongate form medicament carrier till the last of the first and second sets of medicament portions are dispensed. Notably, the roller grips operate in a manner similar to a mangle, wherein the roller grips squeeze the used elongate sheets therethrough together. Alternatively, the roller grips act against a plate and thus squeeze each elongate sheet through either side of the plate. Specifically, the pair of roller grips compress the regions for storing medicament dose portions in the elongate form medicament carrier. As the roller grips are operated, the used elongate sheets are channelled through a gap in walls of the medicament dispenser that surround the exit region from the rollers. Once through the gap, the used elongate sheets move aided by a degree of rigidity and collects in the waste space. The waste space and entry point to the waste space are designed in a manner to urge the elongate sheet to coil in on itself as further portions of the elongate sheets are fed through. Furthermore, during insertion of the elongate form medicament carrier into the medicament dispenser, the unsplit elongate sheet is initially assembled into the medicament dispenser or cartridge by securing part of the central portion thereof around a post proximate to the roller grips.

According to an embodiment, the medicament dispenser comprises a pair of bobbins comprising a first bobbin and a second bobbin, the pair of bobbins configured to wind the split elongate sheet of the elongate form medicament carrier onto the pair of bobbins, starting with the first inner end of the split elongate sheet on the first bobbin and the second inner end of the split elongate sheet on the second bobbin, and continuing to wind first and second portions of the split elongate sheet onto the respective first and second bobbins after dispensing doses from the first and second sets of medicament portions respectively. In particular, the first inner end of the split elongate sheet is coupled to the first bobbin, and the second inner end of the split elongate sheet is coupled with the second bobbin, such that when a medicament portion from each of the first and second set of medicament portions is dispensed, the portion of the split elongate sheet that has been peeled apart from the unsplit elongate sheet is wound around the pair of bobbins. Herein, the pair of bobbins are capable of a rotation motion to aid winding of the split elongate sheet.

According to another embodiment, the medicament dispenser comprises a pair of rollers comprising a first roller and a second roller, the first and second roller having roller grips and being configured to wind the split elongate sheet of the elongate form medicament carrier into a second waste space of the medicament dispenser, starting with the first inner end of the split elongate sheet on the first roller and the second inner end of the split elongate sheet on the second roller, and continuing to wind first and second portions of the split elongate sheet into the second waste space of the medicament dispenser after dispensing doses from the first and second sets of medicament portions respectively. Notably, the first and second roller having roller grips direct the split elongate sheet of the elongate form medicament carrier into the second waste space configured in the medicament dispenser above the at least one receiving station. Herein, the first roller is coupled to the first inner end of the split elongate sheet and the second roller is coupled to the second inner end of the split elongate sheet. The second waste space is configured in a manner that it can accommodate a substantial portion of split elongate sheet of the elongate form medicament carrier till the last of the first and second sets of medicament portions are dispensed.

In an implementation of the present disclosure, the medicament dispenser comprises the take-up spool and the pair of bobbins employed to wind up the unsplit elongate sheet and split elongate sheet respectively. In such implementation, the first bobbin and the second bobbin are driven by a mechanism which coordinates their rotation with the rotation of the take-up spool. Specifically, the mechanism coordinating the rotation ensures the coordinated rotation of the take-up spool and the pair of bobbins such that for every actuation of the medicament dispenser, a single distinct medicament dose portion from each of the first and second sets of medicament dose portions is dispensed by peeling apart the split elongate sheet and the unsplit elongate sheet.

It will be appreciated that the medicament dispenser comprises the actuating means (such as a button or slider) that the patient employs to release the medicament dose portions from the elongate form medicament carrier. The actuating means is operable to trigger the dispensing mechanism, and specifically, the coordinated rotation of the take-up spool and the pair of bobbins, wherein upon rotation, the take-up spool winds the unsplit elongate sheet and the pair of bobbins wind the split elongate sheet. Consequently, due to such winding, the unsplit elongate sheet and split elongate sheet are peeled apart to release each one of the first and second set of medicament dose portions into the outlet. Subsequently, the patient may use suction to receive the medicament dose portions, thereby effecting administering thereof.

Optionally, an elongate form medicament carrier may be inserted into a medicament dispenser of the disclosure during manufacture. In an exemplary process, the first portion of the elongate form medicament carrier is wound onto a first feed spool and the second portion of the elongate form medicament carrier is wound onto a second feed spool.

The first inner end of the split elongate sheet is lifted and attached to an axle of the first bobbin and the second inner end of the split elongate sheet is lifted and attached to an axle of the second bobbin. Such process may be carried out on a carriage with spindles that allows the feed spools and bobbins to be positioned for transfer to a unit of the medicament dispenser. The central portion of the unsplit elongate sheet is dragged by a moving spindle to a position corresponding to the take up spool. As the feed spools and bobbins are brought up to the unit, the moving spindle feeds a short section of the central portion into a peg of the take-up spool and other spindles arrange for the other parts of the elongate form medicament carrier to be fed onto the receiving station bobbin(s) and blade(s).

In an embodiment, the elongate form medicament carrier is assembled into a cartridge. The cartridge is designed to insert into a body of the medicament dispenser. The cartridge may comprise the feed spools, the take-up spool and the bobbin(s). The cartridge may further comprise the capstan(s) and blades(s).

Pursuant to embodiments of the present disclosure, discussed herein after are mechanisms driving the dispensing mechanism (specifically, optionally, the take-up spool and the pair of bobbins) ensuring the release of the medicament dose portions from the elongate form medicament carrier. Herein, in an instance when the elongate form medicament carrier is implemented as a peelable blister strip form medicament carrier, the release of the medicament dispenser comprises a peeler for peeling apart the peelable blister strip form medicament carrier. Specifically, the peeler separates the split elongate sheet from the unsplit elongate sheet to release the medicament dose portion contained in the first and second set of multiple distinct pockets defined between the split elongate sheet and the unsplit elongate sheet.

Optionally, said peeler includes a lid driver for pulling apart said unsplit elongate sheet and said split elongate sheet of a pocket that has been received at the opening station. Notably, the lid driver refers to the mechanism employed in the medicament dispenser to release the medicament dose portions from the elongate form medicament carrier. Specifically, the lid driver refers to the mechanism used to pull apart the lid elongate sheet and the base elongate sheet to release the medicament dose portions from the elongate form medicament carrier.

Optionally, the lid driver comprises the first and/or second bobbin (as described herein above as the pair of bobbins). As aforementioned, the pair of bobbins are configured to wind the split elongate sheet thereon starting with the first inner end and the second inner end of the split elongate sheet. Notably, such winding of the split elongate sheet onto the bobbins enables peeling of the split elongate sheet from the unsplit elongate sheet. The lid driver is operable to provide rotation motion to the first and/or second bobbin, which enables the winding of the split elongate sheets onto the bobbins. Furthermore, said bobbin comprises a wheel on which the split elongate sheet is wound up, said wheel being arranged to progressively collapse as the split elongate sheet becomes wound around it to provide an overall approximately constant effective winding diameter. As aforementioned, the pair of bobbins are configured to wind the split elongate sheet thereon starting with the first inner end and the second inner end of the split elongate sheet. It will be understood that as the unsplit elongate sheet winds on the bobbins, the winding diameter of the bobbin will increase. Therefore, the bobbins are provided with the wheels thereon, wherein the wheels are arranged to progressively collapse, in order to effect a reduction in the diameter of the bobbins.

Consequently, such reduction compensates for the increase in diameter due to winding of the split elongate sheet, thereby provided an overall approximately constant effective winding diameter. In an example, the wheel is implemented using a flexible material, wherein the flexible material is operable to undergo compression to effect the reduction in diameter, and wherein the compression force is exerted due to the wound split elongate sheet.

Optionally, the medicament dispenser additionally comprises control means to control the movement of said lid driver, in order to control the length of blister strip peeled thereby. Specifically, the control means is employed to control the movement of components inside the medicament dispenser (such as, the take-up spool, the pair of bobbins). Optionally, the control means is coupled with the actuating means, as described above, that is used by the patient to start the dispensing mechanism of the medicament dispenser. More optionally, the control means is triggered by the actuating means.

Optionally, said control means comprises a lid driver clutch.

Optionally, the lid driver clutch controls movement of the lid driver by a) a friction coupling or b) a ratchet coupling. As mentioned above, the lid driver provides the rotation motions to the pair of bobbins winding the split elongate sheet. Therefore, such rotation motion is provided to the lid driver by the lid driver clutch. Specifically, the control means employs the lid driver clutch to impart rotation motion to the lid driver, wherein the lid driver transfers that rotation motion to the pair of bobbins. If a length of lid elongate sheet would be advanced out of step with the corresponding length of base elongate sheet, the clutch comes into effect to slip, so as to only transfer that rotation motion needed for the two lengths of elongate to remain in step. In an instance, the lid driver clutch engages with the lid driver by way of a friction coupling, wherein a surface (such as, a clutch disk) of the lid driver clutch comes in contact with the lid driver and engages therewith due to frictional surfaces to provide rotation motion. In another instance, the lid driver clutch engages with the lid driver by way of ratchet coupling, wherein the lid driver comprises angled teeth thereon, in which a tooth or a claw of the lid driver clutch is engaged to provide the rotation motion.

Optionally, a base elongate clutch controls movement of the take-up spool by a) a friction coupling or b) a ratchet coupling. Notably, the take-up spool is operable to wind the unsplit elongate sheet thereon by undergoing a rotation motion, wherein the rotation motion is imparted to the take-up spool by the base elongate clutch. The base elongate clutch comes into effect to slip in a way analogous to the lid elongate clutch. In an instance, the base elongate clutch engages with the take-up spool by way of a friction coupling, wherein a surface (such as, a clutch disk) of the base elongate clutch comes in contact with the take-up spool and engages therewith due to frictional surfaces to provide rotation motion. In another instance, the base elongate clutch engages with the take-up spool by way of ratchet coupling, wherein the take-up spool comprises angled teeth thereon, in which a tooth or a claw of the base elongate clutch is engaged to provide the rotation motion.

Optionally, the medicament dispenser additionally comprises a guide for guiding the unsplit elongate sheet and split elongate sheet along separate paths subsequent to their peeling apart. Notably, the guide is employed to guide the split elongate sheet towards the said pair of bobbins and the unsplit elongate sheet towards the take-up spool.

Optionally, the lid driver clutch allows the indexer to move relative to the lid driver when a prescribed coupling force is exceeded. Optionally, the base elongate clutch allows the indexer to move relative to the take-up spool when a prescribed coupling force is exceeded. Notably, the indexer is coupled to the lid driver clutch and the elongate base clutch in a manner that whenever a force higher than the coupling force is received on any one of the lid driver clutch and the elongate base clutch, such force is interpreted as a release of the medicament dose portions and therefore, the number shown by the indexer is changed.

Optionally, the medicament dispenser additionally comprises chambers for housing said plural medicament carriers prior to opening, and the lid elongate sheet and base elongate sheet components thereof subsequent to opening. Specifically, the medicament dispenser comprises empty spaces therein, wherein additional elongate form medicament carrier can be stored to be used in the medicament dispenser when the existing elongate form medicament carrier employed in the medicament dispenser is expended.

Optionally, any or all components of the dispensing mechanism are drivable by an electronic drive system. Specifically, the medicament dispenser may comprise an electronic drive system housed therein coupled with a power source (such as a battery), wherein the electronic drive system may drive the components such as release and optionally, may further drive the rotation of the components such as the take-up spool and the pair of bobbins.

Optionally, the medicament dispenser additionally comprises an electronic data management system. Optionally, such electronic data management system comprises control instructions for the electronic drive system. Furthermore, optionally, the electronic data management system may store a count of the administered medicament dose portions, details of the medicament actives in the first and second set of medicament dose portions, timings when the medicament dose portions are to be administered.

Optionally, the medicament dispenser is in a reloadable form. Specifically, the medicament dispenser is configured in a manner that a second elongate form medicament carrier is loaded into the medicament dispenser when the existing elongate medicament form carrier is expended.

Optionally, the medicament dispenser comprises a body; a holder, shaped to fit within said body and movable relative to said body; and receivable by said holder, a reload cassette containing one elongate form medicament carrier. Specifically, the reload cassette is insertable into the holder after removal of the existing cassette carrying the existing elongate form medicament carrier.

Optionally, the medicament dispenser is in kit of parts form. Specifically, the kit comprises the body, the holder and the reload cassette, wherein the user may load the reload cassette into the holder to engage the elongate form medicament carrier with the medicament dispenser and may start the administration of the medicament dose portions thereafter.

DETAILED DESCRIPTION OF THE DRAWINGS

Figure 1B:
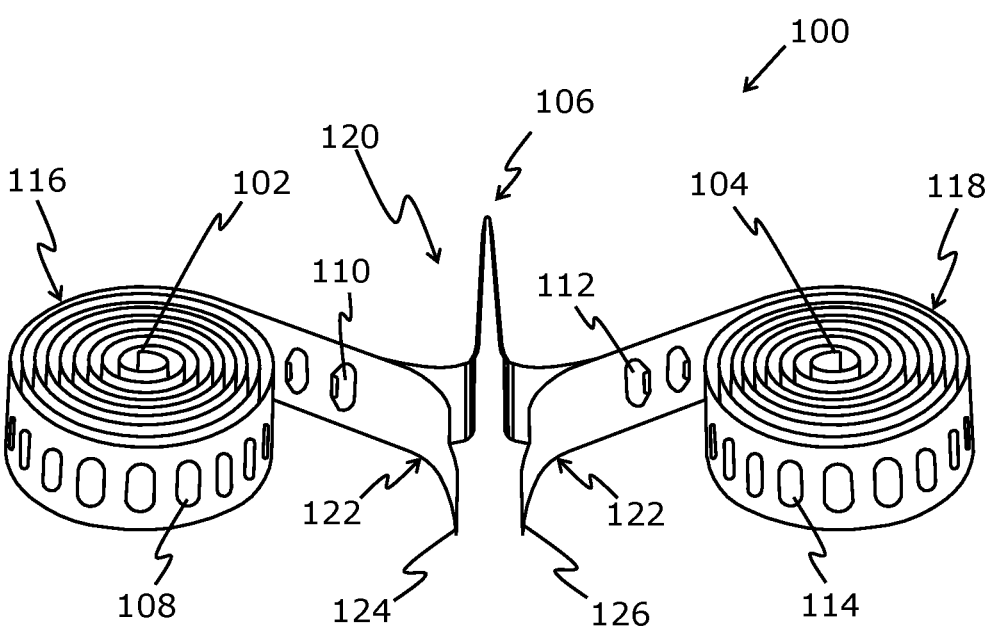

Referring to FIGS. 1A and 1B, illustrated are perspective views of an elongate form medicament carrier 100, in accordance with different embodiments of the present disclosure. The elongate form medicament carrier 100 having a first end 102, a second end 104, and a central portion 106 extending across the width of the elongate form medicament carrier, and carrying multiple distinct medicament dose portions, depicted as the medicament dose portions 108, 110, 112, and 114. The medicament dose portions consist of a first set of medicament dose portions, depicted as medicament dose portions 108 and 110, and a second set of medicament dose portions, depicted as medicament dose portions 112 and 114. The first set of medicament dose portions 108 and 110 are distributed in a first portion 116 of the elongate form medicament carrier 100 between the first end 102 and the central portion 106 of the elongate form medicament carrier 100. The second set of medicament dose portions 112 and 114 are distributed in a second portion 118 of the elongate form medicament carrier 100 between the second end 104 and the central portion 106 of the elongate form medicament carrier 100. Although shown with a tight bend, the central portion 106 is a continuous portion linking the first portion 116 with the second portion 118 of the elongate form medicament carrier 100.

Furthermore, the elongate form medicament carrier 100, as illustrated in FIGS. 1A and 1B, is implemented as a combination of unsplit elongate sheet 120 and split elongate sheet 122. Herein, the central portion of the split elongate sheet 122 is divided to provide a first inner end 124 and a second inner end 126 of the split elongate sheet 122. The first inner end 124 and second inner end 126 are not secured to the unsplit elongate sheet 120.

Moreover, in the elongate form medicament carrier 100 as illustrated in FIG. 1A, the split elongate sheet 122 is implemented as a lid elongate sheet, and the unsplit elongate sheet 120 is a base elongate sheet comprising the medicament dose portions 108, 110, 112, and 114.

Alternatively, in the elongate form medicament carrier 100 as illustrated in FIG. 1B, the unsplit elongate sheet 120 is implemented as the lid elongate sheet, and the split elongate sheet 122 is the base elongate sheet comprising the medicament dose portions 108, 110, 112, and 114.

It may be understood by a person skilled in the art that FIGS. 1A and 1B illustrate simplified implementations of the elongate form medicament carrier 100, for sake of clarity, which should not unduly limit the scope of the claims herein. The person skilled in the art will recognize many variations, alternatives, and modifications of embodiments of the present disclosure.

Figure 2A:
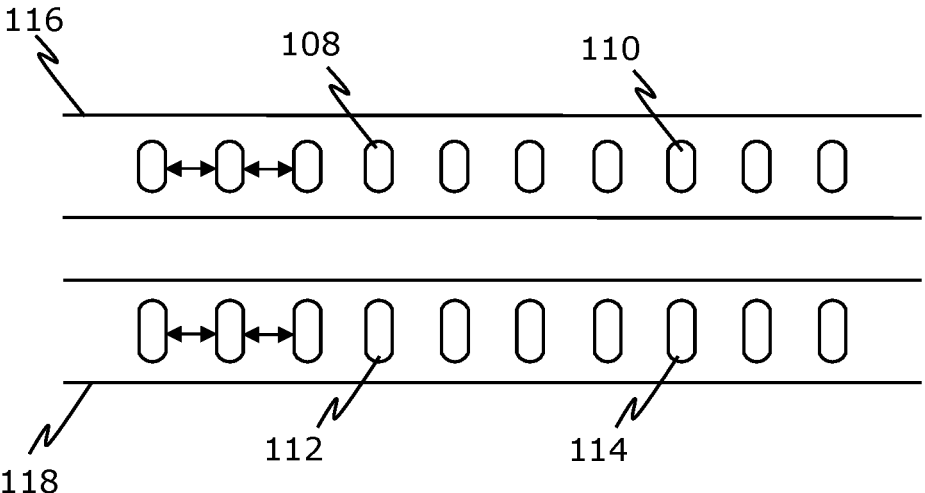
FIGS. 2A and 2B are front views of first portion and second portion of the elongate form medicament carrier, in accordance with different embodiments of the present disclosure.
Figure 2B:
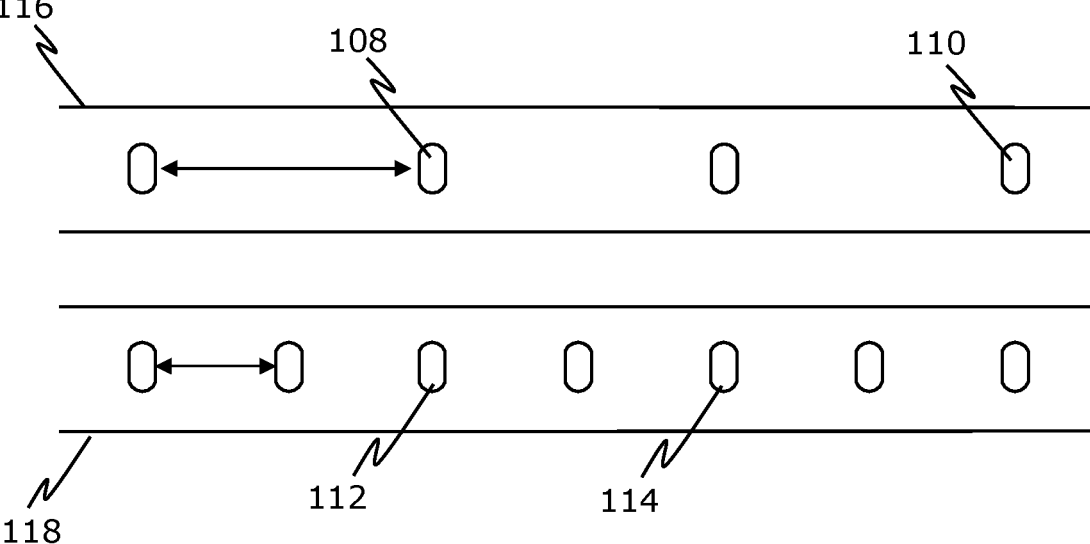

Referring to FIGS. 2A and 2B, illustrated are front views of first portion 116 and second portion 118 of the elongate form medicament carrier (depicted as elongate form medicament carrier 100 in FIG. 1), in accordance with different embodiments of the present disclosure. The first portion 116 of the elongate form medicament carrier 100 comprises a first set of medicament dose portions, such as the medicament dose portions 108 and 110. The second portion 118 of the elongate form medicament carrier 100 comprises a second set of medicament dose portions, such as the medicament dose portions 112 and 114. The multiple distinct medicament dose portions of each of the first portion 116 and the second portion 118 of the elongate form medicament carrier 100 are uniformly spaced.

As illustrated in FIG. 2A, the spacing of the multiple distinct medicament dose portions of the first portion 116 of the elongate form medicament carrier 100 is equivalent to the spacing of the multiple distinct medicament dose portions of the second portion 118 of the elongate form medicament carrier 100.

As illustrated in FIG. 2B, the spacing of the multiple distinct medicament dose portions of the first portion 116 of the elongate form medicament carrier 100 is different from the spacing of the multiple distinct medicament dose portions of the second portion 118 of the elongate form medicament carrier 100.

Figure 3:
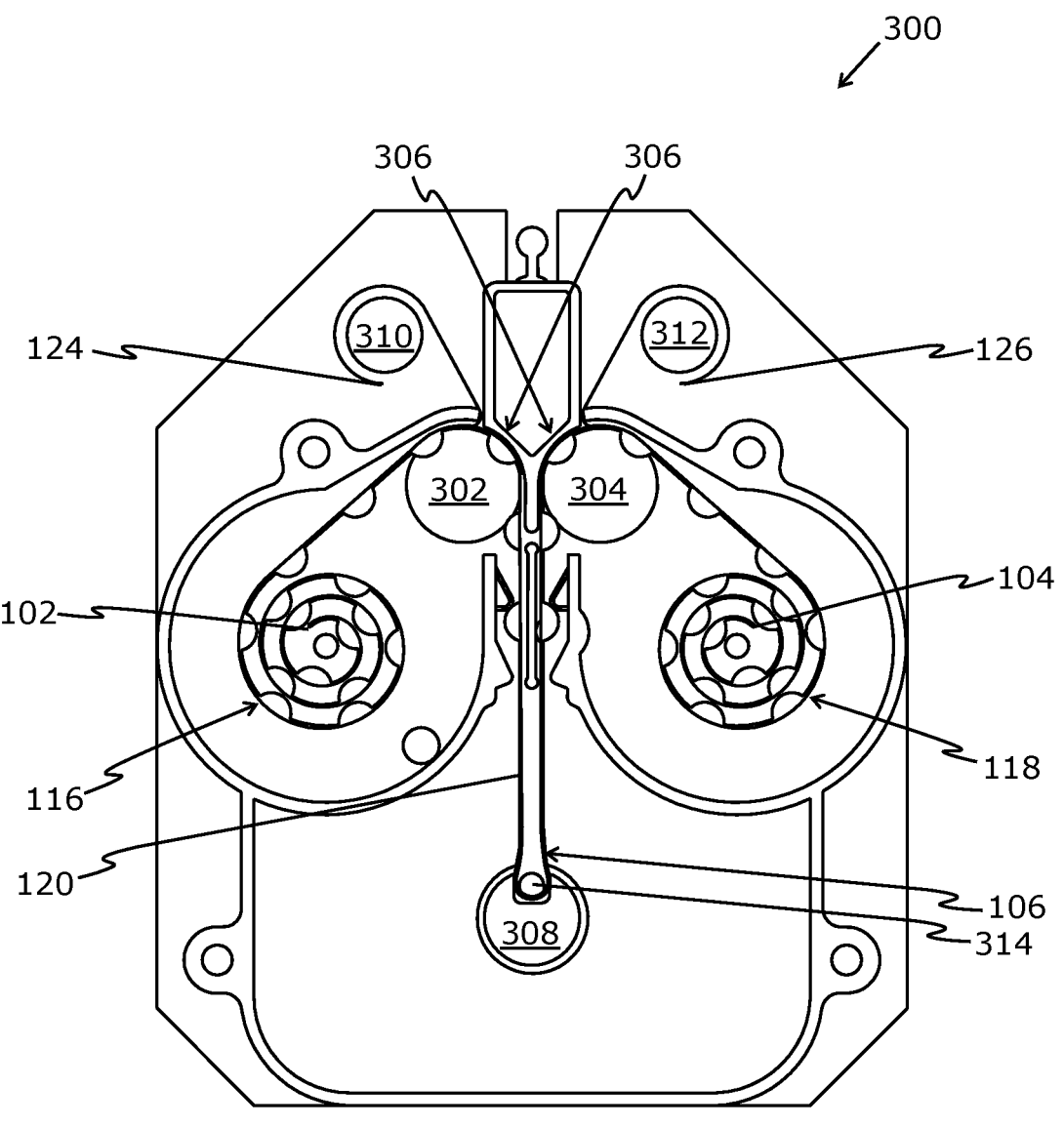
FIGS. 3 and 4 are sectional views of a medicament dispenser, in accordance with different embodiments of the present disclosure.

Referring to FIG. 3, illustrated is a sectional view of a medicament dispenser 300, in accordance with an embodiment of the present disclosure. The medicament dispenser 300 comprises a supply of drug, the supply of drug consisting of one elongate form medicament carrier (such as the elongate form medicament carrier 100 explained in FIG. 1). The medicament dispenser 300 having a dispensing mechanism which is adapted to operate, upon each actuation of the medicament dispenser 300, to dispense a single distinct medicament dose portion from each of said first and second sets of medicament dose portions. The first set of medicament dose portions is distributed in a first portion 116 of the elongate form medicament carrier 100 between the first end 102 and the central portion 106 of the elongate form medicament carrier 100. The second set of medicament dose portions is distributed in a second portion 118 of the elongate form medicament carrier 100 between the second end 104 and the central portion 106 of the elongate form medicament carrier 100. The dispensing mechanism comprises at least one receiving station, depicted as a first capstan 302 and a second capstan 304, that comprise regularly distributed recesses to receive the pockets respectively of the first portion 116 and the second portion 118 of the elongate form medicament carrier 100. The dispensing mechanism further comprises a release for releasing a distinct medicament dose portion from each of the portions 116 and 118 of the elongate form medicament carrier 100. The dispensing mechanism further comprises outlets 306, positioned to be in communication with the distinct medicament dose portions releasable by said release to enable their dispensing to the patient. The dispensing mechanism further comprises at least one indexer (not shown) for individually indexing the distinct medicament dose portions of each of the portions of the elongate form medicament carrier 100.

As shown in FIG. 3, the medicament dispenser 300 further comprises a take-up spool 308 configured to wind the unsplit elongate sheet 120 onto the take-up spool 308 as the take-up spool 308 is rotated, starting with the central portion 106 and continuing to wind the first portion 116 and second portion 118 of the unsplit elongate sheet 120 onto the take-up spool 308 after dispensing doses from the first and second sets of medicament portions respectively. Furthermore, the central portion 106 of the elongate form medicament carrier 100 is secured to the take-up spool 308 by a peg 314.

The medicament dispenser, as illustrated in FIG. 3, further comprises a pair of bobbins comprising a first bobbin 310 and a second bobbin 312, the pair of bobbins configured to wind the split elongate sheet 122 of the elongate form medicament carrier 100 thereon, starting with the first inner end 124 of the split elongate sheet 122 on the first bobbin 310 and the second inner end 126 of the split elongate sheet 122 on the second bobbin 312, and continuing to wind first and second portions of the split elongate sheet 122 onto the respective first bobbin 310 and second bobbin 312 after dispensing doses from the first and second sets of medicament portions respectively.

It may be understood by a person skilled in the art that FIG. 3 illustrates a simplified implementation of the medicament dispenser 300, for sake of clarity, which should not unduly limit the scope of the claims herein. The person skilled in the art will recognize many variations, alternatives, and modifications of embodiments of the present disclosure.

Figure 4:
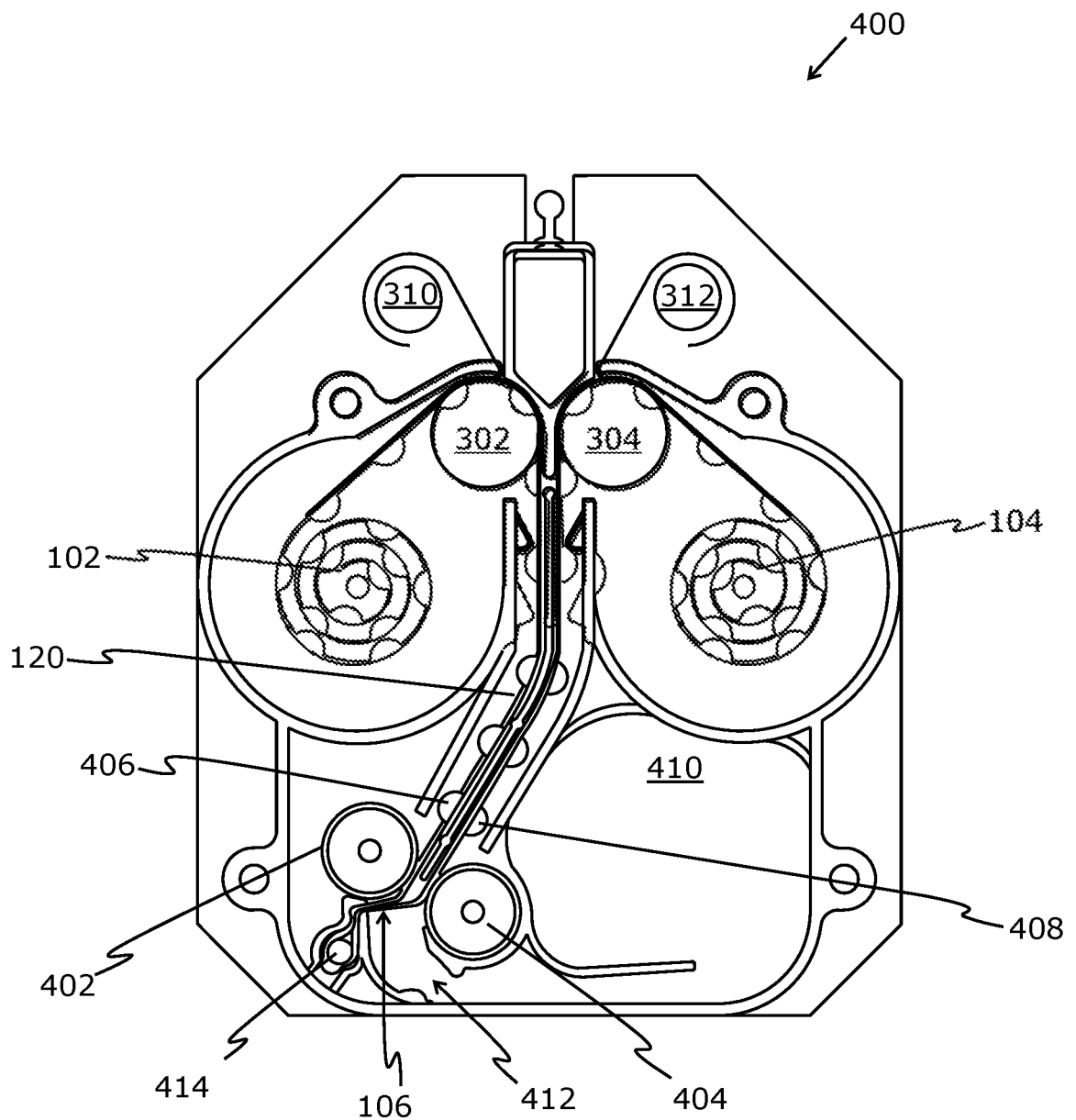

Referring to FIG. 4, illustrated is a sectional view of the medicament dispenser 400, in accordance with another embodiment of the present disclosure. FIG. 4 is similar to FIG. 3, except that it has a different mechanism for collecting used portions of the unsplit elongate sheet. The medicament dispenser 400 comprises a supply of drug, the supply of drug consisting of one elongate form medicament carrier (such as the elongate form medicament carrier 100 explained in FIG. 1). The medicament dispenser 400 has a dispensing mechanism which is adapted to operate, upon each actuation of the medicament dispenser 400, to dispense a single distinct medicament dose portion from each of said first and second sets of medicament dose portions. In accordance with illustrated embodiment of the medicament dispenser, the medicament dispenser 400 comprises a roller with roller grips 402 and 404 configured to compress the regions, such as the regions 406 and 408, for storing medicament dose portions and wind the unsplit elongate sheet 120 into a waste space 410 of the medicament dispenser 400, starting with the central portion 106 and continuing to wind the first and second portions of the unsplit elongate sheet into the waste space after dispensing doses from the first and second sets of medicament portions respectively. In operation, as the roller grips 402 and 404 are operated, the unsplit elongate sheet 120, optionally after undergoing compression, is channelled through a gap 412 in walls of the medicament dispenser 400 that surround the exit region from the roller grips 402 and 404. The waste space 410 and the gap 412 are designed in a manner to ensure that the unsplit elongate sheet 120 coils in on itself as further portions thereof are fed through. Optionally, the medicament dispenser 400 further comprises a peg 414 to secure the central portion 106 of the elongate form medicament carrier there-around.

Figure 5:
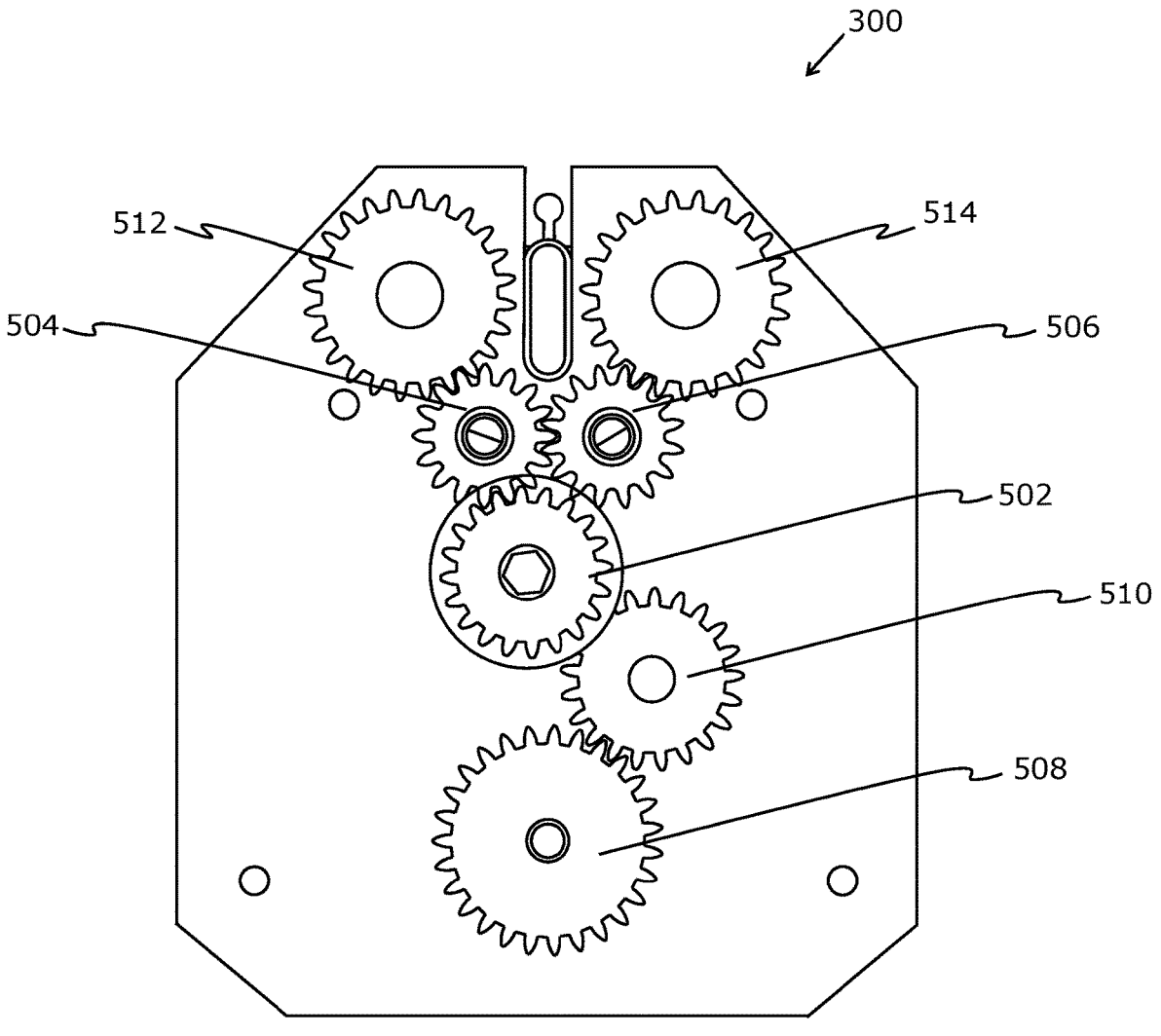
FIG. 5 is a sectional view of a medicament dispenser depicting a gearing arrangement driving the dispensing mechanism of the medicament dispenser, in accordance with an embodiment of the present disclosure.

Referring to FIG. 5, illustrated is a sectional view of a medicament dispenser 300 (as depicted in FIG. 3) depicting a gearing arrangement driving the dispensing mechanism of the medicament dispenser 300, in accordance with an embodiment of the present disclosure. Herein, the gearing arrangement comprises a plurality of gears driven through a lid driver gear 502. The lid driver gear 502 is coupled with a plurality of capstan gears, specifically a first capstan gear 504 mutually coupled to a second capstan gear 506, wherein the first capstan gear 504 drives the first capstan 302 and second capstan gear 506 drives the second capstan 304 as depicted in FIG. 3. Furthermore, the lid driver gear 502 is coupled to a take-up spool gear 508 (wherein, the take-up spool gear 508 drives the take-up spool 308 depicted in FIG. 3) using a connecting gear 510. Moreover, the first capstan gear 504 is coupled to a first bobbin gear 512 (driving the first bobbin 310) and the second capstan gear 506 is coupled to a second bobbin gear 514 (driving the second bobbin 312). Herein the dispensing mechanism comprises a lid driver connected to the lid driver gear 502, wherein the first capstan gear 504 and the second capstan gear 506 are driven by the lid driver which coordinates its rotation with the rotation of the take-up spool gear 508 and with the first bobbin gear 512 and the second bobbin gear 514.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A medicament dispenser comprising:

a supply of drug, the supply of drug consisting of an elongate form medicament carrier, the elongate form medicament carrier comprising:

a first end, a second end, and a central portion extending across a width of the elongate form medicament carrier;

multiple distinct medicament dose portions consisting of a first set of medicament dose portions and a second set of medicament dose portions, wherein the first set of medicament dose portions is distributed in a first portion of the elongate form medicament carrier between the first end and the central portion of the elongate form medicament carrier, the first set of medicament dose portions containing a medicament active, or a mixture of medicament actives, wherein the second set of medicament dose portions is distributed in a second portion of the elongate form medicament carrier between the second end and the central portion of the elongate form medicament carrier, the second set of medicament dose portions containing a medicament active, or a mixture of medicament actives, and wherein the dose portions in the second set of medicament dose portions are different from the dose portions in the first set of medicament dose portions; and a split elongate sheet substantially secured to an unsplit elongate sheet, the unsplit elongate sheet and the split elongate sheet each having respective central portions corresponding to the central portion of the elongate form medicament carrier, first portions corresponding to the first set of medicament dose portions and second portions corresponding to the second set of medicament dose portions, wherein the unsplit elongate sheet and the split elongate sheet have first and second ends corresponding to the first and second ends of the elongate form medicament carrier, wherein the central portion of the split elongate sheet is divided to provide a first inner end and a second inner end of the split elongate sheet, and wherein the first inner end and second inner end are not secured to the unsplit elongate sheet; and a dispensing mechanism adapted to operate, upon each actuation of the medicament dispenser, to dispense a single distinct medicament dose portion from each of said first and second sets of medicament dose portions, said dispensing mechanism comprising:

a. at least one receiving station receiving portions of the elongate form medicament carrier respectively carrying each of the first and second sets of medicament dose portions;

b. a release for releasing a distinct medicament dose portion from each of the portions of the elongate form medicament carrier respectively carrying each of the first and second sets of medicament dose portions, wherein the release comprises a blade, punch/piercer and/or bobbins;

c. an outlet, positioned to be in communication with the distinct medicament dose portions releasable by said release to enable dispensing of the distinct medicament dose portions to a patient; and d. at least one indexer for individually indexing the distinct medicament dose portions of each of the portions of the elongate form medicament carrier respectively carrying each of the first and second sets of medicament dose portions, wherein the at least one indexer comprises a mechanical or digital dose counter(s).

2. The medicament dispenser according to claim 1, further comprising a take-up spool configured to wind the unsplit elongate sheet onto the take-up spool as the take-up spool is rotated, starting with the central portion of the unsplit elongate sheet and continuing to wind the first and second portions of the unsplit elongate sheet onto the take-up spool after dispensing doses from the first and second sets of medicament dose portions respectively.

3. The medicament dispenser according to claim 2, in which the central portion of the unsplit elongate sheet is secured to the take-up spool.

4. The medicament dispenser according to claim 1, further comprising a roller with roller grips configured to wind the unsplit elongate sheet into a waste space of the medicament dispenser, starting with the central portion of the unsplit elongate sheet and continuing to wind the first and second portions of the unsplit elongate sheet into the waste space after dispensing doses from the first and second sets of medicament dose portions respectively.

5. The medicament dispenser according to claim 1, further comprising a pair of bobbins comprising a first bobbin and a second bobbin, the pair of bobbins configured to wind the split elongate sheet of the elongate form medicament carrier onto the pair of bobbins, starting with the first inner end of the split elongate sheet on the first bobbin and the second inner end of the split elongate sheet on the second bobbin, and continuing to wind the first and second portions of the split elongate sheet onto the respective first and second bobbins after dispensing doses from the first and second sets of medicament dose portions respectively.

6. The medicament dispenser according to claim 1, further comprising a pair of rollers comprising a first roller and a second roller, the first and second rollers having roller grips and being configured to wind the split elongate sheet of the elongate form medicament carrier into a waste space of the medicament dispenser, starting with the first inner end of the split elongate sheet on the first roller and the second inner end of the split elongate sheet on the second roller, and continuing to wind the first and second portions of the split elongate sheet into the waste space of the medicament dispenser after dispensing doses from the first and second sets of medicament dose portions respectively.

7. The medicament dispenser according to claim 1, wherein either the split elongate sheet is a lid elongate sheet and the unsplit elongate sheet is a base elongate sheet, or the split elongate sheet is a base elongate sheet and the unsplit elongate sheet is a lid elongate sheet.

8. The medicament dispenser according to claim 7, wherein a first set and a second set of multiple distinct pockets are defined between the base elongate sheet and the lid elongate sheet and contain medicament respectively consisting of the first set of medicament dose portions and the second set of medicament dose portions, wherein said first set of pockets is spaced along a length of the first portion of the elongate form medicament carrier and the second set of pockets is spaced along a length of the second portion of the elongate form medicament carrier.

9. The medicament dispenser according to claim 8, wherein the multiple distinct pockets are formed in the base elongate sheet, and the lid elongate sheet is hermetically sealed to the base elongate sheet except in a region of the multiple distinct pockets and the first and second inner ends of the split elongate sheet, in such a manner that the lid elongate sheet and the base elongate sheet can be peeled apart.

10. The medicament dispenser according to claim 1, wherein the dose portions in the second set of medicament dose portions differ from the dose portions in the first set of medicament dose portions in that the dose portions in the second set of medicament dose portions contain a medicament active, or a mixture of medicament actives that is different from that in the first set of medicament dose portions.

11. The medicament dispenser according to claim 1, in which the first portion of the elongate form medicament carrier is substantially the same size and shape as the second portion of the elongate form medicament carrier.

12. The medicament dispenser according to claim 1, wherein the multiple distinct medicament dose portions of each of the first portion and the second portion of the elongate form medicament carrier are uniformly spaced.

13. The medicament dispenser according to claim 12, wherein the spacing of the multiple distinct medicament dose portions of the first portion of the elongate form medicament carrier is equivalent to the spacing of the multiple distinct medicament dose portions of the second portion of the elongate form medicament carrier.

14. The medicament dispenser according to claim 12, wherein lengths of the central portions are greater than the spacing of the multiple distinct medicament dose portions of both the first and the second portions of the elongate form medicament carrier.

15. The medicament dispenser according to claim 1, wherein the medicament dose portions are in powdered or solid form.

16. The medicament dispenser according to claim 15, wherein each medicament dose portion of each portion of the elongate form medicament carrier comprises a single active medicament component.

17. The medicament dispenser according to claim 16, wherein the single active medicament component is selected from the group consisting of vilanterol, salmeterol, fluticasone propionate, formoterol, budesonide and olodaterol and salts or solvates thereof.

18. The medicament dispenser according to claim 17, wherein each of the first set of medicament dose portions comprises a bronchodilator as the active medicament component and each of the second set of medicament dose portions comprises an anti-inflammatory as the active medicament component.

19. The medicament dispenser according to claim 18, wherein said bronchodilator is a long-acting beta-agonist and/or a long-acting muscarinic receptor agonist and said anti-inflammatory is a steroid.

20. The medicament dispenser according to claim 1, wherein each medicament dose portion of at least one set of medicament dose portions comprises plural active medicament components.

* * * * *